(12) United States Patent
Ericson et al.

(10) Patent No.: US 8,980,542 B2
(45) Date of Patent: Mar. 17, 2015

(54) ARGININE-CONTAINING COMPOSITIONS AND METHODS FOR TREATING RED BLOOD CELLS

(75) Inventors: Daniel G. Ericson, Rochester, MN (US); Jeffrey A. Thompson, Shorewood, MN (US)

(73) Assignee: Viacell, LLC, Ham Lake, MN (US)

( * ) Notice: Subject to any disclaimer, the term of this patent is extended or adjusted under 35 U.S.C. 154(b) by 402 days.

(21) Appl. No.: 13/028,856

(22) Filed: Feb. 16, 2011

(65) Prior Publication Data

US 2011/0256522 A1      Oct. 20, 2011

Related U.S. Application Data

(60) Provisional application No. 61/338,263, filed on Feb. 16, 2010, provisional application No. 61/370,713, filed on Aug. 4, 2010.

(51) Int. Cl.
| | | |
|---|---|---|
| *A01N 1/02* | (2006.01) | |
| *A61K 35/18* | (2006.01) | |
| *A61K 31/198* | (2006.01) | |
| *A61K 31/7004* | (2006.01) | |

(52) U.S. Cl.
CPC .............. *A61K 35/18* (2013.01); *A01N 1/0226* (2013.01); *A61K 31/198* (2013.01); *A61K 31/7004* (2013.01)
USPC .......................................................... 435/2

(58) Field of Classification Search
CPC ................................................... A01N 1/0226
See application file for complete search history.

(56) References Cited

U.S. PATENT DOCUMENTS

| | | | |
|---|---|---|---|
| 3,847,738 A | 11/1974 | Brake et al. | |
| 4,386,069 A | 5/1983 | Estep | |
| 4,432,750 A | 2/1984 | Estep | |
| 4,572,899 A | 2/1986 | Walker et al. | |
| 4,585,735 A | 4/1986 | Meryman et al. | |
| 4,675,185 A | 6/1987 | Kandler et al. | |
| 4,695,460 A | 9/1987 | Holme | |
| 4,710,532 A | 12/1987 | Hull et al. | |
| 4,769,318 A | 9/1988 | Hamasaki et al. | |
| 4,774,088 A | 9/1988 | Vora | |
| 4,812,310 A | 3/1989 | Sato et al. | |
| 4,853,370 A | 8/1989 | Ecanow et al. | |
| 4,870,002 A | 9/1989 | Kiel | |
| 4,871,718 A * | 10/1989 | Carniglia .......................... 514/23 |
| 4,880,786 A | 11/1989 | Sasakawa et al. | |
| 4,889,943 A | 12/1989 | Kawamura et al. | |
| 4,961,928 A | 10/1990 | Holme et al. | |
| 5,248,506 A | 9/1993 | Holme et al. | |
| 5,250,303 A | 10/1993 | Meryman et al. | |
| 5,487,971 A | 1/1996 | Holme et al. | |
| 5,601,972 A | 2/1997 | Meryman | |
| 5,769,839 A | 6/1998 | Carmen et al. | |
| 5,789,151 A | 8/1998 | Bitensky et al. | |
| 5,906,915 A | 5/1999 | Payrat et al. | |
| 6,150,085 A | 11/2000 | Hess et al. | |
| 6,159,942 A | 12/2000 | St. Cyr et al. | |
| 6,447,987 B1 | 9/2002 | Hess et al. | |
| 7,687,468 B2 | 3/2010 | St. Cyr et al. | |
| 7,723,017 B2* | 5/2010 | Bitensky et al. .................. 435/2 |
| 2002/0187990 A1* | 12/2002 | Parks et al. .................... 514/269 |
| 2003/0148256 A1 | 8/2003 | Payrat et al. | |
| 2003/0228564 A1* | 12/2003 | Edrich et al. ...................... 435/2 |
| 2004/0106094 A1 | 6/2004 | Payrat et al. | |
| 2004/0192553 A1 | 9/2004 | Kurauchi et al. | |
| 2005/0074743 A1 | 4/2005 | Purmal et al. | |
| 2005/0208462 A1 | 9/2005 | Bitensky et al. | |
| 2006/0292134 A1 | 12/2006 | Stohs | |
| 2007/0111191 A1 | 5/2007 | St. Cyr et al. | |
| 2007/0178434 A1 | 8/2007 | Natan et al. | |
| 2007/0298406 A1 | 12/2007 | Martorell Pena et al. | |
| 2009/0239208 A1 | 9/2009 | Mayaudon et al. | |
| 2011/0229871 A1 | 9/2011 | Ericson | |

FOREIGN PATENT DOCUMENTS

| | | |
|---|---|---|
| DE | 37 11 699 A1 | 11/1988 |
| EP | 1 869 977 A1 | 12/2007 |
| JP | 61-012626 A | 1/1986 |
| WO | WO 2004/105483 A1 | 12/2004 |
| WO | WO 2006/088455 A1 | 8/2006 |
| WO | WO2008/089337 * | 7/2008 |
| WO | WO 2011/103177 A1 | 8/2011 |
| WO | WO 2011/103179 A1 | 8/2011 |

OTHER PUBLICATIONS

"Acid-citrate-dextrose," [online]. Wikipedia, the free encyclopedia, [retrieved on Jun. 16, 2010]. Retrieved from the Internet: <URL: http://en.wikipedia.org/wiki/Acid-citrate-dextrose>; 2 pgs; last modified Apr. 11, 2010.

Akerblom et al., "Restoration of Defective Oxygen-transport Function of Stored Red Blood Cells by Addition of Inosine," *Scand. J. Clin. Lab. Invest.*, 1968; 21(3): 245-248.

"Anticoagulation and Preservation" [online]. Bloodindex, [retrieved on Jun. 16, 2010]. Retrieved from the Internet: <URL: http://www.bloodindex.net/blood_anticoagulation_preservation.php>; 4 pgs.

Arun et al., "Decreased Hemolysis and Lipid Peroxidation in Blood during Storage in the Presence of Nicotinic Acid," *Vox Sang.*, 1999; 76(4): 220-225.

Bartlett et al., "Changes in the Phosphate Compounds of the Human Red Blood Cell During Blood Bank Storage," *J. Clin. Invest.*, Jan. 1960; 39(1): 56-61.

(Continued)

*Primary Examiner* — Sandra Saucier

(74) *Attorney, Agent, or Firm* — Mueting, Raasch & Gebhardt, P.A.

(57) ABSTRACT

Blood storage and/or rejuvenating compositions that include D-ribose and an arginine (e.g. L-arginine, D-arginine, or a combination thereof) are disclosed herein. Such compositions can be useful in methods for treating (e.g., storing and/or rejuvenating) red blood cells.

47 Claims, 5 Drawing Sheets

(56) References Cited

OTHER PUBLICATIONS

Becker, "Phosphoribosylpyrophosphate Synthetase and the Regulation of Phosphoribosylpyrophosphate Production in Human Cells," *Prog. Nucleic Acid Res. Mol. Biol.*, 2001; 69: 115-148.
Beutler et al., "The in vivo regeneration of red cell 2,3 diphosphoglyceric acid (DPG) after transfusion of stored blood," *J. Lab. Clin. Med.*, Aug. 1969; 74(2): 300-304.
"Blood components," [online]. Diaglab, Cornell University [retrieved on Jun. 15, 2010]. Retrieved from the Internet: <URL: http:www.diaglab.vet.cornell.edu/clinpath/modules/coags/comp.htm>; 3 pgs.
"Blood FAQ," American Association of Blood Banks [online] [retreived on Aug. 18, 2011]. Available online. <URL: http://www.aabb.org/resources/bct/pages/bloodfaq.aspx>, 3 pgs.
Bunn et al., "Hemoglobin Function in Stored Blood," *J. Clin. Invest.*, 1969; 48(2): 311-321.
Chen et al., "Solubility Enhancement of Nucleosides and Structurally Related Compounds by Complex Formation," *Pharm. Res.*, Mar. 1994; 11(3): 398-401.
Chiu et al., "Lipid Peroxidation in Human Red Cells," *Semin. Hematol.*, Oct. 1989; 26(4): 257-276.
"Circular of Information: For the Use of Human Blood and Blood Components," American Association of Blood Banks et al., Aug. 2009, revised Dec. 2009, 48 pgs.
Corwin et al., "The CRIT Study: Anemia and blood transfusion in the critically ill—Current clinical practice in the United States," *Crit. Care Med.*, Jan. 2004; 32(1): 39-52.
Dawson et al., "Blood Preservation XXIX: Pyruvate Maintains Normal Red Cell 2,3-DPG for Six Weeks of Storage in CPD-Adenine," *Transfusion*, Mar.-Apr. 1980, 20(2):218-223.
Dawson et al., "Blood Preservation 33. Phosphate Enhancement of Ribose Maintenance of 2,3-DPG and ATP," *Transfusion*, Mar.-Apr. 1981; 21(2): 215-218.
Dawson et al., "Blood preservation 42: Improvement of Ascorbate's Ability to Maintain 2,3-DPG with Inosine," *Transfusion*, May-Jun. 1981; 21(3): 285-290.
Dawson et al., Blood preservation 50: Red Cell 2,3 DPG Maintenance in CPD-Adenine Stored Blood by Several Mechanisms, The Red Cell: $5^{th}$ Annual Arbor Conf., 1981:643-660.
Dawson, "Preservation of Red Blood Cells for Transfusion," *Hum. Pathol.*, Mar. 1983; 14(3): 213-217.
Dawson et al., "Dihydroxyacetone, pyruvate, and phosphate effects on 2,3 DPG and ATP in citrate-phosphate-dextrose-adenine blood preservation," *Transfusion*, Jul.-Aug. 1984; 24(4): 327-329.
Dawson et al., "Control of Red Cell 2,3-DPG Levels in vitro and a Proposal for in vivo Control in Response to Hypoxia and Metabolic Demand," *Prog. Clin. Biol. Res.*, 1985; 195: 349-368.
Delivoria-Papadopoulos et al., "Oxygen-Hemoglobulin Dissociation Curves: Effect of Inherited Enzyme Defects of the Red Cell," *Science*, Aug. 8, 1969;165(893): 601-602.
Deneke et al., "Regulation of cellular glutathione," *Am. J. Physiol. Lung Cell. Mol. Physiol.*, 1989; 257: L163-L173.
Department of Health and Human Services, Food and Drug Administration, "REJUVESOL®, Red Blood Cell Processing Solution," enCyte™ Systems, Inc.; 32 pages. Oct. 5, 1998.
Dormandy, "The Autoxidation of Red Cells," *Br. J. Haematol.*, May 1971; 20(5): 457-461.
Dumaswala et al., "Glutathione Loading Prevents Free Radical Injury in Red Blood Cells After Storage," *Free Rad. Res.*, Nov. 2000; 33(5): 517-529.
Dumaswala et al., "Glutathione protects chemokine-scavenging and antioxidative defense functions in human RBCs," *Am. J. Physiol. Cell Physiol.*, 2001; 280(4): 867-873.
Elfath, "Is it time to focus on preserving the functionality of red blood cells during storage?" *Transfusion*, Sep. 2006; 46:1469-70.
"FDA Licensure for Conversion to CP2D/AS-3 Anticoagulant/Additive Systems," Pall Corporation, East Hills, NY, 2004, 22 pgs.
Fitzgerald et al., "Transfusing red blood cells stored in citrate phosphate dextrose adenine-1 for 28 days fails to improve tissue oxygenation in rats," *Crit. Care Med.*, May 1997; 25(5): 726-732.

The Free Online Medical Dictionary, 2012 (http://medical-dictionary.thefreedictionary.com/pyruvate), 3 pgs.
Halliwell et al., "Oxygen toxicity, oxygen radicals, transition metals and disease," *Biochem. J.*, Apr. 1984; 219(1): 1-14.
Hawkes et al., "Heart surgery patients put in danger by using 14-day-old blood," *TimesOnline* (London), Mar. 24, 2008 [retrieved on Oct. 13, 2008].Retrieved from the Internet:<URL:http://www.timesonline.co.uk/tol/life_and_style/health/article3607486>; 2 pgs.
Hébert et al., "A Pilot Trial Evaluating the Clinical Effects of Prolonged Storage of Red Cells," *Anesth. Analg.*, May 2005; 100(5): 1433-1438.
Hess et al., "Buffering and dilution in red blood cell storage," *Transfusion*, Jan. 2006; 45:50-54.
Hillyer et al., *Blood banking and transfusion medicine: basic principles and practice*, Elsevier, London, England, 2007; pp. 185-187.
"Inosine," [online] Wikipedia, the free encyclopedia, [retrieved on Feb. 11, 2010]. Retrieved from the Internet: <URL: http://en.wikipedia.org/wiki/Inosine>; 3 pgs.
International Search Report and Written Opinion of the International Searching Authority, issued May 26, 2011, by the PCT, Patent Application No. PCT/US2011/025069, filed Feb. 16, 2011, 11 pgs.
Jain, "Evidence for membrane lipid peroxidation during the in vivo aging of human erythrocytes," *Biochim. Biophys. Acta*, Jan. 1988; 937(2): 205-210.
Jensen, "Red blood cell pH, the Bohr effect, and other oxygenation-linked phenomena in blood $O_2$ and $CO_2$ transport," *Acta Physiol. Scand.*, Nov. 2004; 182(3): 215-227.
Jóźwik et al., "Antioxidant defence of red blood cells and plasma in stored human blood," *Clin. Chim. Acta*, Nov. 28, 1997; 267(2): 129-142.
Kanias et al., "Biopreservation of red blood cells—the struggle with hemoglobin oxidation," *FEBS J.*, Jan. 2010; 277(2): 343-356. Available online Nov. 26, 2009.
Knight et al., "Lipid peroxidation in stored red cells," *Transfusion*, May 1992; 32(4): 354-357.
Koch et al., "Duration of Red-Cell Storage and Complications After Cardiac Surgery," *N. Engl. J. Med.*, Mar. 20, 2008; 358:1229-1239.
Marik et al., "Effect of stored-blood transfusion on oxygen delivery in patients with sepsis," *JAMA*, Jun. 16, 1993; 269(23): 3024-3029.
Material Safety Data Sheet, Fenwal, 4368, Version 2, Print date: Jan. 14, 2011, 5 pgs.
McCullough, *Transfusion Medicine*, $2^{nd}$ edition, London, England, 2005, cover page, title page and table of contents only, 4 pgs.
Medline Abstract, 75128511, Petrich et al., "Influence of ribose on 2,3-diphosphoglycerate concentrations in human erythrocytes," 1975: 1 pg.
Moore, "Long-Teen Storage and Preservation of Red Blood Cells," *Biotechnology of Blood*, Stoneham, MA, Chap. 2:31-46, 1982.
"Nucleoside," [online] Wikipedia, the free encyclopedia, [retrieved on Feb. 11, 2010]. Retrieved from the Internet: <URL: http://en/wikipedia.org/wiki/Nucleoside>; 2 pgs, last modified Feb. 10, 2010.
Oski et al., "The In Vitro Restoration of Red Cell 2,3-Diphosphoglycerate Levels in Banked Blood," *Blood*, 1971; 37(1): 52-58.
Petrich et al., "Der Einfluss von Ribose auf die 2,3-Diphosphoglycerat-Konzentration menschlicher Erythrozyten," *Blut*, 1995; 30:175-182). (English translation included (12 pgs).
Prankerd, T., "Revival of Stored Blood with Guanosine," *The Lancet*, Apr. 21, 1956; 6921:469-471.
Raat et al., "The effect of storage time of human red cells on intestinal microcirculatory oxygenation in a rat isovolemic exchange model," *Crit. Care Med.*, Jan. 2005; 33(1): 39-45.
Simon, E., "Adenine and Purine Nucleosides in Human Red Cell preservation: A Review," *Transfusion*, Nov.-Dec. 1967; 7:395-400.
U.S. Food and Drug Administration, "Anticoagulant Citrate Phosphate Double Dextrose (CP2D) & Additive Solution 3 (AS-3)—Summary Basis of Approval," [online, retrieved on Jun. 16, 2010]. Retrieved from the Internet: <URL: http://www.fda.gov/BiologicsBloodVaccines/BloodBloodProducts/ApprovedProducts/NewDrugApplicationsNDAs/ucm082820.htm>, 3 pgs.
Valeri et al., "The survival, function, and hemolysis of human RBCs stored at 4° C. in additive solution (AS-1, AS-3, or AS-5) for 42 days

(56) References Cited

OTHER PUBLICATIONS and then biochemically modified, frozen, thawed, washed, and stored at 4° C. in sodium chloride and glucose solution for 24 hours," *Transfusion*, Nov. 2000; 40(11):1341-1345.

Valeri et al., "Restoration in vivo of erythrocyte adenosine triphosphate, 2,3-diphosphoglycerate, potassium ion, and sodium ion concentrations following the transfusion of acid-citrate-dextrose-stored human red blood cells," *J. Lab. Clin. Med.*, May 1969; 73(5): 722-733.

Vamvakas et al., "Length of storage of transfused red cells and postoperative morbidity in patients undergoing coronary artery bypass graft surgery," *Transfusion*, Jan. 2000; 40(1): 101-109.

van de Watering et al., "Effects of storage time of red blood cell transfusions on the prognosis of coronary artery bypass graft patients," *Transfusion*, Oct. 2006; 46(10): 1712-1718.

Walsh et al., "Does the storage time of transfused red blood cells influence regional or global indexes of tissue oxygenation in anemic critically ill patients?" *Crit. Care Med.*, Feb. 2004; 32(2): 364-371.

Zallen et al., "Age of Transfused Blood is an Independent Risk Factor for Postinjury Multiple Organ Failure," *Am. J. Surg.*, Dec. 1999; 178(6): 570-572.

Zimmer, "Restitution of myocardial adenine nucleotides: acceleration by administration of ribose," *J. Physiol.* (Paris), 1980; 76(7): 769-775.

Zimmer, "The oxidative pentose phosphate pathway in the heart: Regulation, physiological significance, and clinical implications," *Basic Res. Cardiol.*, Jul.-Aug. 1992; 87(4): 303-316.

Ignarro et al., "Nitric Oxide Donors and Cardiovascular Agents Modulating the Bioactivity of Nitric Oxide: An Overview," *Circulation Research*, 2002; 90:21-28.

\* cited by examiner

ARGININE-CONTAINING COMPOSITIONS AND METHODS FOR TREATING RED BLOOD CELLS

This application claims the benefit of U.S. Provisional Application Nos. 61/338,263, filed Feb. 16, 2010, and 61/370,713, filed Aug. 4, 2010, both of which are incorporated herein by reference in their entireties.

BACKGROUND

Whole blood is a living tissue that circulates through the heart, arteries, veins and capillaries, carrying nourishment, electrolytes, antibodies, heat and oxygen to the body tissues. Whole blood includes red blood cells (RBCs), white blood cells and platelets suspended in a proteinaceous fluid termed blood plasma. If blood is treated to prevent clotting and permitted to stand in a container, RBCs will settle to the bottom of the container, the plasma will remain on top and the white blood cells will form a layer on top of the RBCs. A centrifuge is commonly used to hasten this separation. The platelet-rich plasma is then removed and placed into a sterile bag for further processing to separate, for example, platelets, clotting factors, albumin, immunoglobulins and the like.

The most important component for the usual transfusion need are the erythrocytes or RBCs, which contain hemoglobin, a complex iron-containing protein that carries oxygen throughout the body and gives blood its red color. The percentage of blood volume that is composed of RBCs is called the "hematocrit." The average hematocrit in the adult male is 47%. There are about one billion RBCs in two or three drops of blood, and, for every 600 RBCs, there are about 40 platelets and one white blood cell.

Manufactured in the bone marrow, RBCs are enucleated, biconcave discs that are continuously being produced, broken down and destroyed. The biconcave disc shape is crucial to the function of RBCs, presenting a maximal surface area for the capture of oxygen in the lungs and its release in the tissue. The cells are flexible and able to bend in order to traverse the tiny tubules of the capillary beds. Since the cells are enucleated and lack mitochondria, they are unable to carry out cellular repair processes and must rely on anaerobic phosphorylation for energy. After an average of 120 days in the circulatory system, the cells are senescent and are phagocytized by circulating monocytes or the fixed macrophages of the reticulo-endothelial system.

RBCs are prepared from whole blood by removing the plasma. When transfused into a patient, the hematocrit is raised while an increase in blood volume is minimized, which is especially important to such patients as those with congestive heart failure. The cells are typically suspended in about half the original volume; the preparation is referred to as packed red cells. Patients benefiting most from transfusions of RBCs include those with chronic refractive anemia from disorders such as kidney failure, malignancies, gastrointestinal bleeding or acute blood loss as from trauma or surgery.

Because patients seldom require all of the components of whole blood; it is the usual practice in blood banks to separate the blood into components and transfuse only that portion needed by the patient for a specific condition or disease. This treatment, referred to as "blood component therapy" allows several patients to benefit from each unit of blood. Unfortunately, the separation of blood components for therapy is detrimental to the RBCs, causing a storage lesion characterized by a decrease in the marker 2,3-diphosphoglycerate (2,3-DPG), an increase in the production of oxygen free radicals and a change in morphology.

Standard solutions for the storage of whole blood include citrate-phosphate-dextrose solution (CPD) and citrate-phosphate-dextrose-adenine solution (CPDA). Citrate or other anticoagulants such as heparin are necessary to prevent clotting. Because blood is a living tissue that maintains metabolic functions even at refrigerated temperatures, it has been considered necessary to provide an energy source such as dextrose. Phosphate ion can be used to buffer the lactate produced from dextrose utilization.

Improvements in cell preservation solutions over the last 15 years have increased the refrigerated shelf life of whole blood or RBCs from 21 to 42 days. After 42 days, the blood is discarded, since many of the cells have become senescent and would be immediately phagocytized upon transfusion into a recipient. Although the red cells may appear to survive in storage for five or six weeks, they rapidly develop storage lesions characterized by hemolysis and/or biochemical and biomechanical changes that can compromise their survival time and their ability to accept, transport, and unload oxygen to the tissue. For that reason, it is desirable to use the whole blood and blood products within three weeks or less of drawing.

The need remains for a solution in which blood cells in whole blood or packed red cell suspensions can be stored for an increased time and survive functionally when transfused into a recipient. The need also remains for a method to rejuvenate blood and RBCs which are functioning sub-optimally.

SUMMARY

Methods of collecting and storing RBCs prior to transfusion continue to be a challenge in improving blood bank practice. RBCs can be stored for 42 days at 4° C., but over this time RBC storage lesions occur despite improvements of anticoagulant solutions and blood additives. Among the most significant storage lesions of RBCs are a) the depletion of 2,3-DPG, resulting in a decrease in the ability of the blood to offload oxygen to tissue leading to an increase in oxygen affinity; b) morphological changes that reduce cell viability, increase fragility, and decrease deformability, impacting the ability of the cell to traverse the microcirculation; and c) the release of biochemical substances that result in fever, cellular damage, and tissue dysfunction. These storage lesions predominantly result from the depletion of cellular energy (i.e., adenosine triphosphate, or ATP) and lactic acid accumulation associated with decreased energy metabolism.

Experimental additive solutions that slow the rate of 2,3-DPG depletion and ATP loss are known. See, for example, Dawson et al., *Prog Clin Biol Res.* 1985; 195:349-68; Dawson et al., *Transfusion* 1984 July-August; 24(4):327-9; Dawson et al., *Hum Pathol.* 1983 March; 14(3):213-7; Dawson et al., *Transfusion* 1981 May-June; 21(3):285-90; and Dawson et al., *Transfusion* 1981 March-April; 21(2):215. These experimental solutions typically include a series of inorganic phosphates and inosine. Although the solutions are capable of maintaining 2,3-DPG levels to some degree, the requirement of the solution constituents created some issues that limited their utility. One issue was the low solubility of inosine, which resulted in a slurry being added to the RBCs that would subsequently require washing the cells prior to transfusion. Another issue is the biochemical progression leading to the formation of the potentially toxic breakdown products such as hypoxanthine and uric acid. Furthermore, the transfusion product must be warmed for one hour prior to transfusion, which impacts the practicality of such an additive solution in current blood banking practice. In preferred embodiments, the blood storage and/or rejuvenating compositions disclosed herein address one or more of these issues.

In one aspect, the present disclosure provides a blood storage and/or rejuvenating composition. In one embodiment, the composition includes D-ribose and L-arginine and/or D-arginine (and preferably L-arginine). Optionally, the composition can further include one or more of sodium pyruvate, an inorganic phosphate, and inosine. In preferred embodiments, the composition is an aqueous solution. Methods of using such compositions are also disclosed.

In another embodiment, the blood storage and/or rejuvenating composition includes: 75 to 1500 mM L-arginine and/or D-arginine (and preferably L-arginine); and 75 to 1500 mM inosine, wherein the composition is an aqueous solution. Optionally, the composition can further include D-ribose at a concentration of, for example, 75 to 1500 mM. Optionally, the composition can further include sodium pyruvate at a concentration of, for example, 75 to 1500 mM. Optionally, the composition can further include an inorganic phosphate at a concentration of, for example, 75 to 1500 mM. When used to store and/or rejuvenate blood, the composition is typically diluted approximately 30-fold to provide a final concentration of 2.5 to 50 mM L-arginine and/or D-arginine (and preferably L-arginine); 2.5 to 50 mM inosine; and optionally 2.5 to 50 mM D-ribose, 2.5 to 50 mM sodium pyruvate, and/or 2.5 to 50 mM inorganic phosphate.

In certain preferred embodiments, the blood storage and/or rejuvenating composition includes: 150 to 900 mM L-arginine and/or D-arginine (and preferably L-arginine); and 150 to 900 mM inosine, and the composition is an aqueous solution. Optionally, the composition can further include D-ribose at a concentration of, for example, 150 to 900 mM. Optionally, the composition can further include sodium pyruvate at a concentration of, for example, 150 to 900 mM. Optionally, the composition can further include an inorganic phosphate at a concentration of, for example, 150 to 900 mM. When used to store and/or rejuvenate blood, the composition is typically diluted approximately 30-fold to provide a final concentration of 5 to 30 mM L-arginine and/or D-arginine (and preferably L-arginine); and 5 to 30 mM inosine; and optionally 5 to 30 mM D-ribose, 5 to 30 mM sodium pyruvate, and/or 5 to 30 mM inorganic phosphate.

In other preferred embodiments, the blood storage and/or rejuvenating composition includes: 300 to 600 mM L-arginine and/or D-arginine (and preferably L-arginine); and 300 to 600 mM inosine, and the composition is an aqueous solution. Optionally, the composition can further include D-ribose at a concentration of, for example, 300 to 600 mM. Optionally, the composition can further include sodium pyruvate at a concentration of, for example, 300 to 600 mM. Optionally, the composition can further include an inorganic phosphate at a concentration of, for example, 300 to 600 mM. When used to store and/or rejuvenate blood, the composition is typically diluted approximately 30-fold to provide a final concentration of 10 to 20 mM L-arginine and/or D-arginine (and preferably L-arginine); and 10 to 20 mM inosine; and optionally 10 to 20 mM D-ribose, 10 to 20 mM sodium pyruvate, and/or 10 to 20 mM inorganic phosphate.

In certain embodiments, the molar ratio of L-arginine to inosine is 0.5:1 to 1.5:1. In other certain embodiments, the molar ratio of L-arginine to inosine is 0.8:1 to 1.2:1. In certain preferred embodiments, the molar ratio of L-arginine to inosine is 1:1.

In another embodiment, the blood storage and/or rejuvenating composition includes: 300 mM L-arginine; 300 mM inosine; 300 mM D-ribose; 300 mM sodium pyruvate; and 300 mM inorganic phosphate, wherein the composition is an aqueous solution. When used to store and/or rejuvenate blood, the composition is typically diluted approximately 30-fold to provide a final concentration of 10 mM L-arginine; 10 mM inosine; 10 mM D-ribose; 10 mM sodium pyruvate; and 10 mM inorganic phosphate.

In certain embodiments, a blood storage and/or rejuvenating composition as described herein can further include one or more of sodium chloride, dextrose, adenine, mannitol, sodium citrate, and citric acid.

For one example, the blood storage and/or rejuvenation composition can be an additive solution that includes L-arginine, inosine, D-ribose, sodium pyruvate, inorganic phosphate, sodium chloride, dextrose, adenine, and mannitol. Such an additive solution is particularly useful for storing and/or rejuvenating blood containing an anticoagulant selected from the group consisting of ACD, CPD, CPDA-1, and combinations thereof.

For another example, the blood storage and/or rejuvenating composition can be an additive solution that includes L-arginine, inosine, D-ribose, sodium pyruvate, inorganic phosphate, sodium chloride, dextrose, adenine, sodium citrate, and citric acid. Such an additive solution is particularly useful for storing and/or rejuvenating blood containing CP2D anticoagulant.

Methods for storing and/or rejuvenating RBCs are described herein. Additional methods are described, for example, in U.S. Patent Application Publication No. 2007/0111191 A1 (St. Cyr et al.), U.S. Pat. No. 7,687,468 (St. Cyr et al.), and copending U.S. patent application Ser. No. 13/028819, entitled "NUCLEOSIDE-CONTAINING COMPOSITIONS AND METHODS FOR TREATING RED BLOOD CELLS", filed the same day herewith.

In another aspect, the present disclosure further provides methods of improving the antioxidant defense of stored RBCs.

In one embodiment, the method includes contacting RBCs with a blood storage and/or rejuvenating composition as described herein.

In another embodiment, the method includes contacting a composition including RBCs and an anticoagulant with an additive solution as described herein, wherein the anticoagulant is selected from the group consisting of ACD, CPD, CPDA-1, and combinations thereof.

In another embodiment, the method includes contacting a composition including RBCs and an anticoagulant with an additive solution as described herein, wherein the anticoagulant is CP2D.

The technology described within this application describes a RBC storage and/or rejuvenating composition that, in preferred embodiments, does not present the solubility difficulties associated with inosine, does not produce a high level of breakdown products, and/or does not require warming of the RBCs prior to transfusion. The storage and/or rejuvenating composition described herein includes a pentose carbohydrate (e.g., D-Ribose) that can serve to aid de novo synthesis and metabolic salvage of purine nucleotides including ATP. The storage and/or rejuvenating composition can also include inorganic phosphate, which can serve as a substrate for phosphorolysis; and/or sodium pyruvate, which can serve as a source for NAD and allow 1,3-diphosphoglycerate to be converted to either 2,3-DPG or 3-phosphoglycerate. In one embodiment, L-arginine is utilized to fully solubilize inosine.

Definitions

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

ACD (Acid Citrate Dextrose) is an anticoagulant and preservative solution, a liter of which is reported to contain 22.0 g trisodium citrate (dihydrate), 8.0 g citric acid (monohydrate), and 24.5 g dextrose (monohydrate) in water.

CPD (Citrate Phosphate Dextrose) is an anticoagulant and preservative solution, a liter of which is reported to contain 26.30 g trisodium citrate (dihydrate), 3.27 g citric acid (monohydrate), 2.22 g sodium dihydrogen phosphate (monohydrate), and 25.5 g dextrose (monohydrate) in water.

CPDA-1 (Citrate Phosphate Dextrose Adenine) is an anticoagulant and preservative solution, a liter of which is reported to contain 26.30 g trisodium citrate (dihydrate), 3.27 g citric acid (monohydrate), 2.22 g sodium dihydrogen phosphate (monohydrate), 31.9 g dextrose (monohydrate), and 0.275 g adenine in water.

CP2D (Citrate Phosphate Double Dextrose) is an anticoagulant and preservative solution, a liter of which is reported to contain 26.30 g trisodium citrate (dihydrate), 3.27 g citric acid (monohydrate), 2.22 g sodium dihydrogen phosphate (monohydrate), and 51.1 g dextrose (monohydrate) in water.

AS1 is an additive solution for use with Citrate Phosphate Dextrose type anticoagulant solutions (e.g., CPD and CPDA-1), 100 ml of which is reported to contain 2.20 g dextrose (monohydrate), 27 mg adenine, 750 mg mannitol, and 900 mg sodium chloride. The additive solution is typically added to RBCs after they are separated from the plasma.

AS3 is an additive solution for use with CP2D anticoagulant solution, 100 ml of which is reported to contain 1.1 g dextrose (anhydrous), 30 mg adenine, 276 mg monobasic sodium phosphate (monohydrate), 410 mg sodium chloride, 588 mg sodium citrate (dihydrate), and 42 mg citric acid (monohydrate). The additive solution is typically added to RBCs after they are separated from the plasma.

AS5 is an additive solution for use with Citrate Phosphate Dextrose type anticoagulant solutions (e.g., CPD and CPDA-1), 100 ml of which is reported to contain 900 mg dextrose (monohydrate), 30 mg adenine, 525 mg mannitol, and 877 mg sodium chloride. The additive solution is typically added to RBCs after they are separated from the plasma.

The above brief description of various embodiments of the present invention is not intended to describe each embodiment or every implementation of the present invention. Rather, a more complete understanding of the invention will become apparent and appreciated by reference to the following description and claims in view of the accompanying drawings. Further, it is to be understood that other embodiments may be utilized and structural changes may be made without departing from the scope of the present invention.

DETAILED DESCRIPTION OF ILLUSTRATIVE EMBODIMENTS

Figure 1:
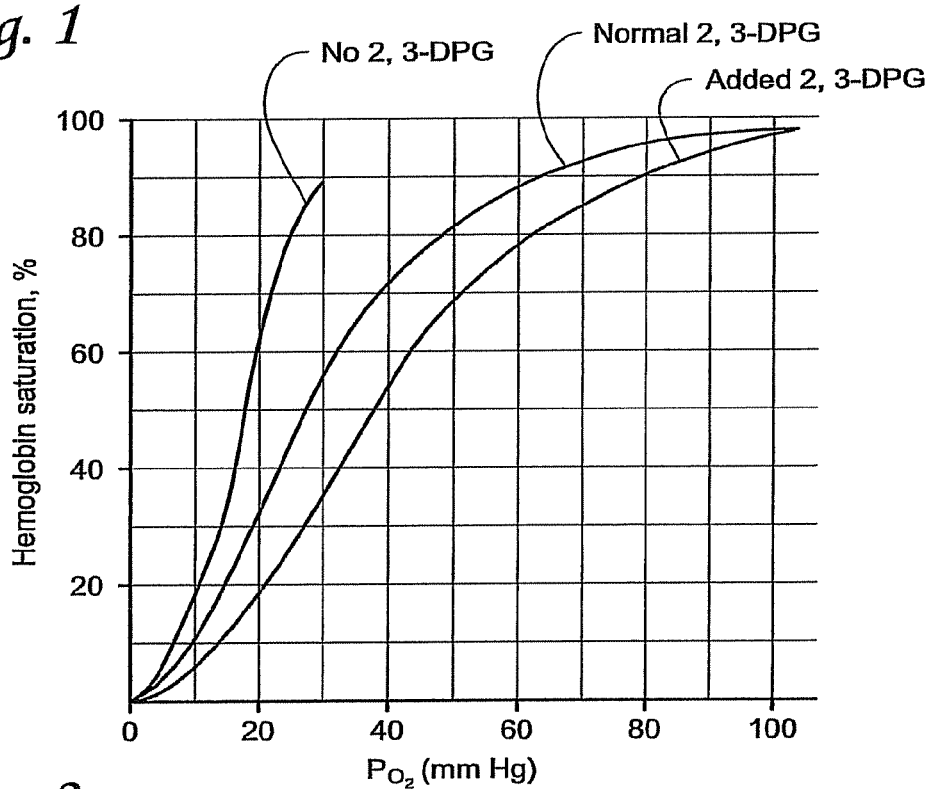
FIG. 1 is a graphical representation of an oxygen dissociation curve showing the effect of 2,3-DPG levels (no 2,3-DPG; normal level of 2,3-DPG; and added 2,3-DPG), with hemoglobin saturation (%) plotted on the y-axis, and $P_{O_2}$ (mm Hg) plotted on the x-axis.
Figure 2:
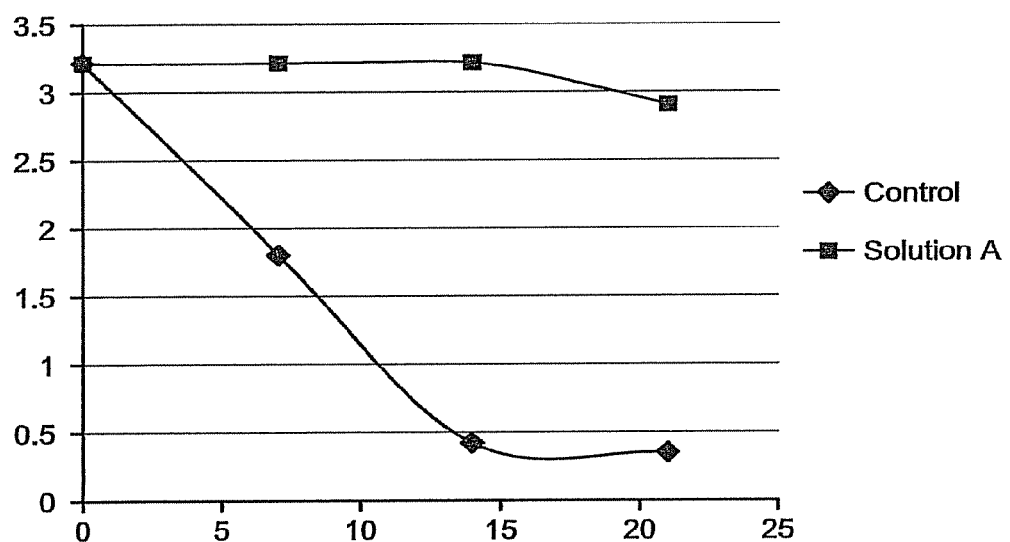
FIG. 2 is a graphical illustration showing 2,3-DPG levels (mmole 2,3-DPG/liter erythrocytes) vs. storage time (days) for human blood using an embodiment of the present invention (Solution A) and a control.
Figure 3:
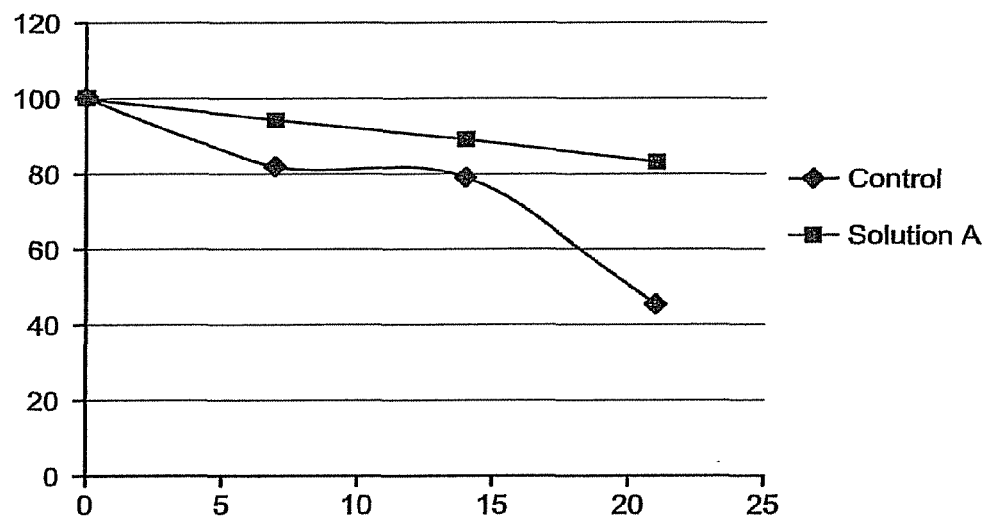
FIG. 3 is a graphical illustration showing ATP levels (ATP, % Baseline) vs. storage time (days) for human blood using an embodiment of the present invention (Solution A) and a control.
Figure 4:
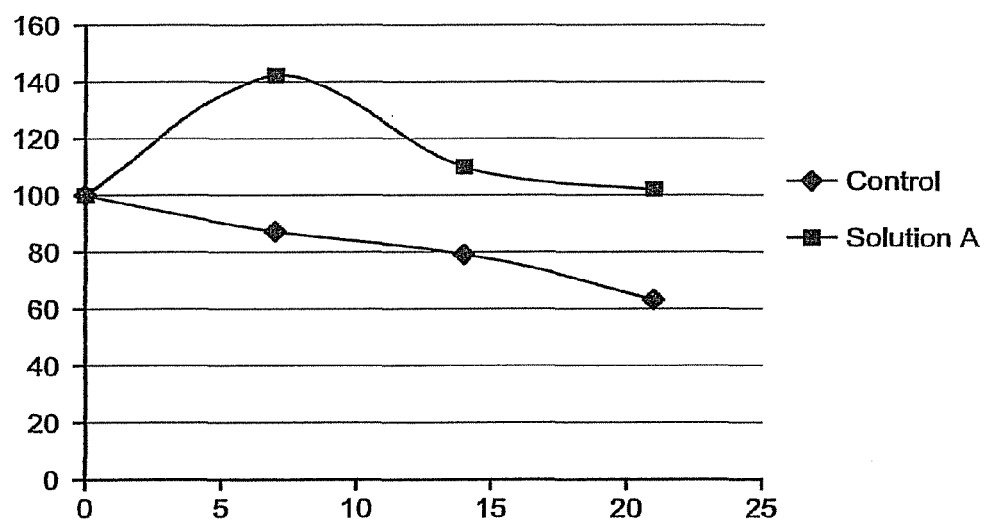
FIG. 4 is a graphical illustration showing reduced glutathione levels (% Baseline) vs. storage time (days) for human blood using an embodiment of the present invention (Solution A) and a control.
Figure 5:
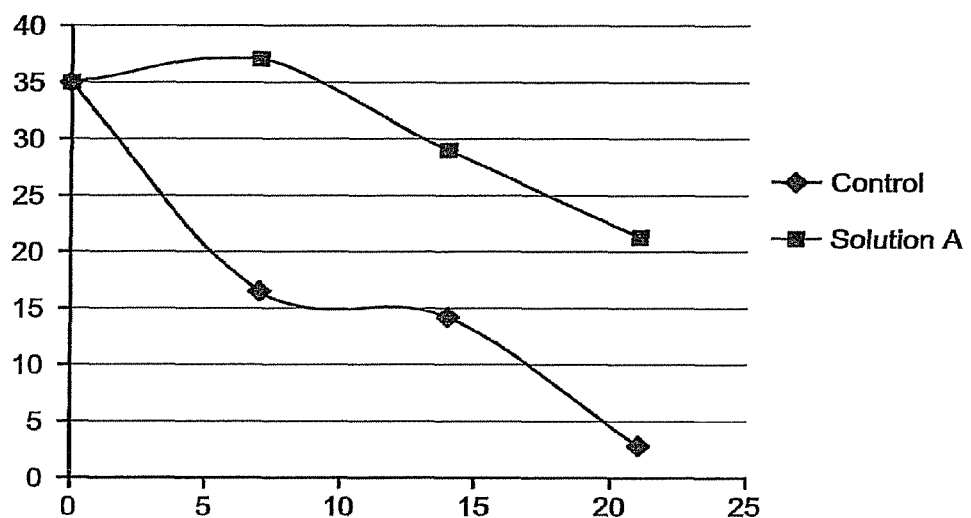
FIG. 5 is a graphical illustration showing P50 levels (mm Hg) vs. storage time (days) for human blood using an embodiment of the present invention (Solution A) and a control.
Figure 6:
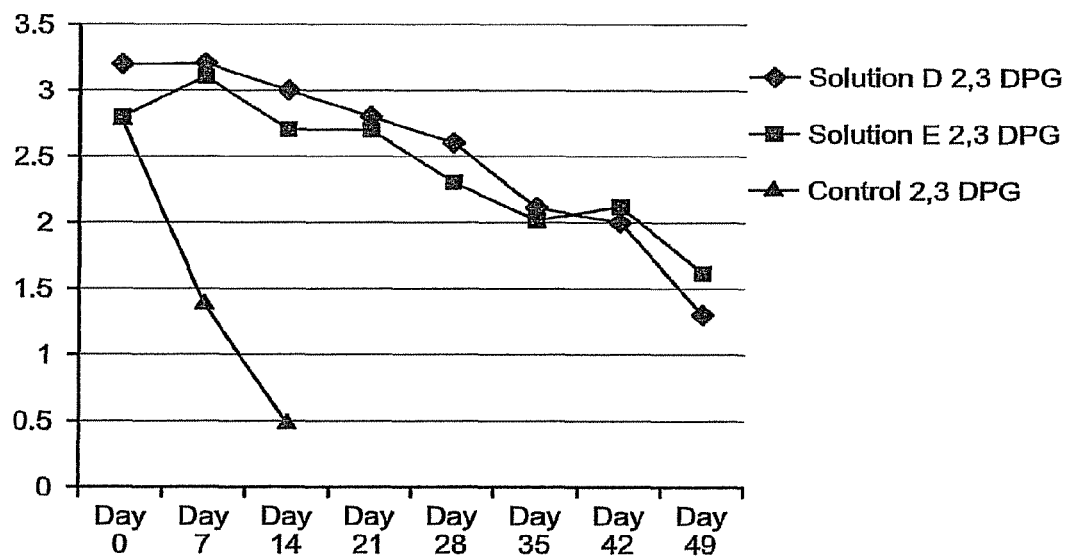
FIG. 6 is a graphical illustration showing 2,3-DPG levels (mmole 2,3-DPG/liter erythrocytes) vs. storage time (days) for human blood using embodiments of the present invention (Solutions D and E) and a control.
Figure 7:
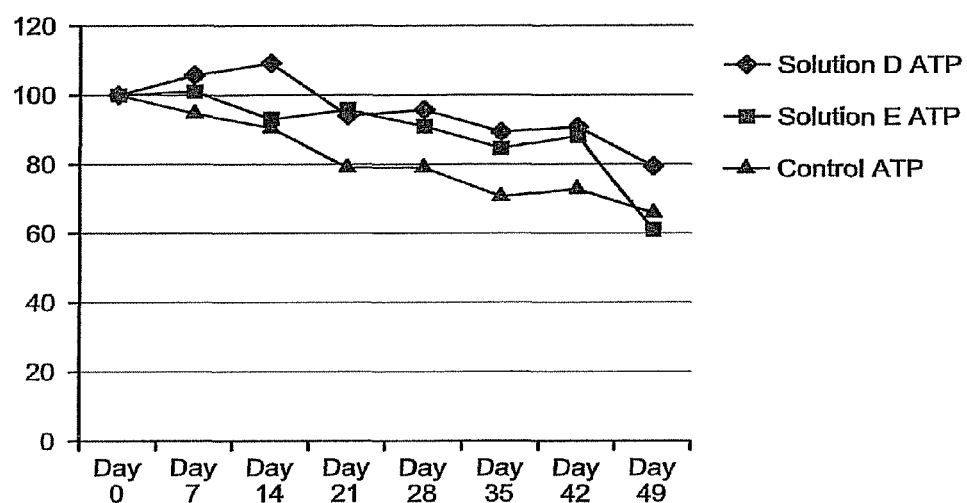
FIG. 7 is a graphical illustration showing ATP levels (ATP, % Baseline) vs. storage time (days) for human blood using embodiments of the present invention (Solutions D and E) and a control.
Figure 8:
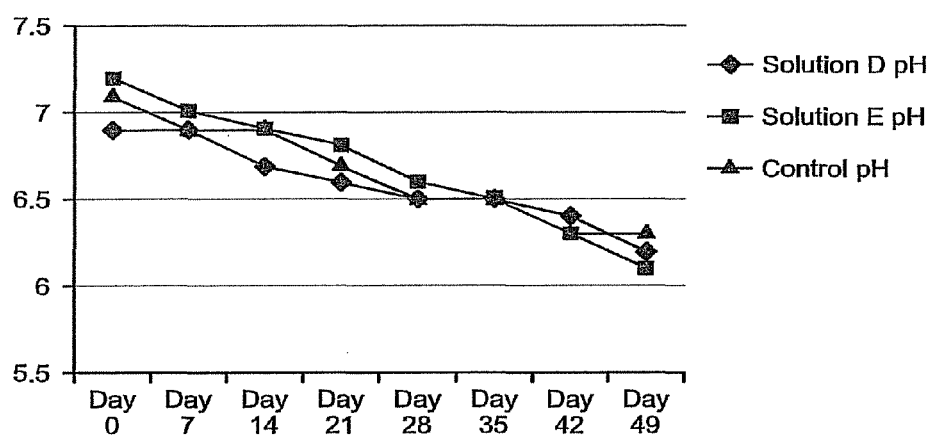
FIG. 8 is a graphical illustration showing pH vs. storage time (days) for human blood using embodiments of the present invention (Solutions D and E) and a control.
Figure 9:
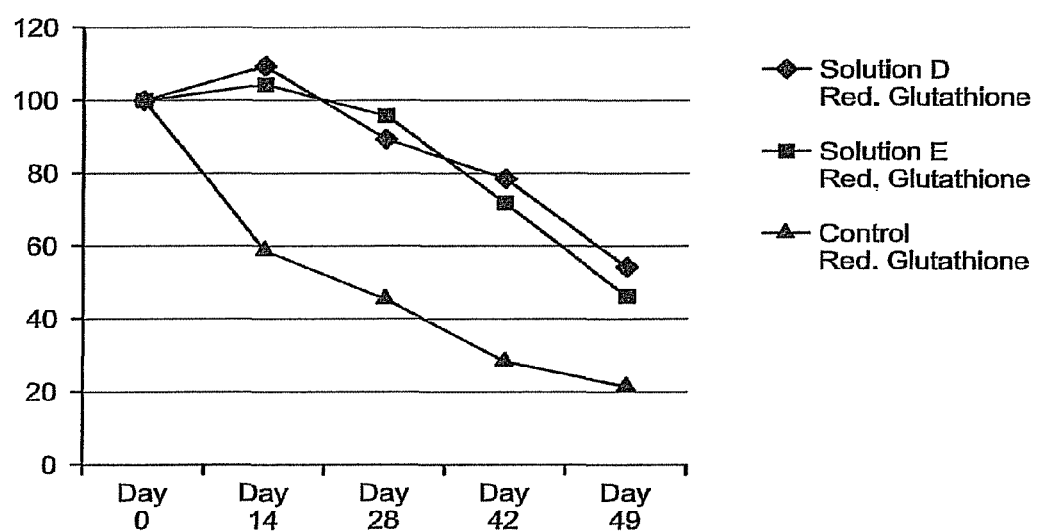
FIG. 9 is a graphical illustration showing reduced glutathione levels (%) vs. storage time (days) for human blood using embodiments of the present invention (Solutions D and E) and a control.

In 1915, blood transfusion was first attempted from a direct donor to a recipient. During the years following World War I, the practice improved with the use of a citrate glucose solution to collect the blood, the use of refrigeration, and blood typing. Then, in the 1960's and 1970's, improvements continued when glass bottle storage was replaced with durable plastic bags, better anticoagulants were developed, and the addition of mannitol and adenine allowed for storage of RBCs for 42 days. See, for example, Bartlett et al., *J. Clin. Invest.* 1960; 39:56; Bunn et al., *J. Clin. Invest.* 1969; 48:311; Akerblom et al., *Scand. J. Clin. Lab. Invest.* 1968; 21:245-248; and Delivoria-Papadopoulos et al., *Science* 1969; 165:601-602. Today, blood is still preserved with various anticoagulant solutions that include adenine and citrate. The blood is stored at 4° C., collected in plasticized blood bags, and discarded if not used within 42 days because RBC viability is largely lost after that time. As RBCs die, the lysed cells release the more durable hemoglobin molecule, which has a low P50, and which presents a barrier to oxygen diffusion. Today some estimate that there are approximately 16 million units of RBCs transfused annually in the United States.

RBCs undergo major biochemical and biomechanical changes during storage that affect their post transfusion performance. Recent epidemiological studies show that the transfusion of older stored blood is associated with increased mortality, serious infections, multi-organ failure, and hospital length of stay. See, for example, Walsh et al., *Crit. Care Med.* 2004; 32:364-371; Van de Watering et al., *Transfusion* 2006; 46:1712-1718; Vamvakas et al., *Transfusion* 2000; 40:101-109; and Hebert et al., *Anesthesia & Analgesia.* 2005; 100: 1433-1438. The RBC storage lesion is evidenced by the loss of 2,3-DPG, the principal organic phosphate of the human erythrocyte. The 2,3-DPG content within the cell correlates with the position of the oxygen-hemoglobin dissociation curve, as reflected by the P50 (the partial pressure of oxygen ($O_2$) at which hemoglobin is 50% saturated). In blood stored under conventional blood bank conditions, the 2,3-DPG level drops sharply, and by 10 days of storage 2,3-DPG levels are only 20-25 percent of their original level. Within 21 days of storage they fall to 10 percent of their initial content (Van de Watering et al., *Transfusion* 2006; 46:1712-1718; and Vamvakas et al., *Transfusion* 2000; 40:101-109.

Storage lesions remain a significant concern and a major focus of research in transfusion medicine. Evidence suggests that storage of RBCs for long periods of time results in reduced oxygen delivery, and transfusion of older blood (i.e., greater than 14-days of storage) has been identified as an independent risk factor for the development of multiple organ failure. See, for example, (Fitzgerald et al., *Crit. Care Med.* 1997; 25:726-732; Malik et al., JAMA, 1993; 269:3024-3029; Raat et al., *Crit. Care Med.*, 2005; 33:39-45; and Zallen et al., *Am. J. Surg.*, 1999; 178:570-572).

Based on the results of early studies (e.g., Van de Watering et al., *Transfusion* 2006; 46:1712-1718; and Vamvakas et al., *Transfusion* 2000; 40:101-109), it has been assumed that 2,3-DPG levels in RBCs are rejuvenated within 24-hours of transfusion. These studies were performed in normal volunteers with no circulatory problems and with normal blood volume. It is not known whether such recovery would occur in patients suffering from severe blood loss, circulatory issues, or problems associated with underlying medical conditions. Further, the inability of transfused RBCs to deliver oxygen to tissue during the critical time in the early hours following transfusion may have a significant impact on clinical outcome. Although certain studies indicate that the age of transfused RBCs has little or no effect on clinical outcomes in certain conditions (e.g., Hebert et al., *Anesthesia & Analgesia*. 2005; 100:1433-1438), others suggest the opposite, showing that the duration of storage of RBCs is associated with adverse outcome (Oski et al., *Blood* 1971; 37:52-58).

A predominance of the literature suggests the development of an RBC storage solution(s) that would limit or reverse storage lesions would be of considerable consequence to transfusion medicine and could help make RBC transfusion safer and more effective. See, for example, Fitzgerald et al., *Crit. Care Med.* 1997; 25:726-732; Malik et al., JAMA, 1993; 269:3024-3029; Raat et al., *Crit. Care Med.*, 2005; 33:39-45; Zallen et al., *Am. J. Surg.*, 1999; 178:570-572; Buetler et al., *J. Lab. Clin. Med.*, 1969; 74:300; and Valerie et al., *J. Lab. Clim. Med.*, 1969; 73:722-733. It is postulated that presently disclosed RBC storage and/or rejuvenating compositions will provide such a restorative benefit.

In one aspect, the present disclosure provides a blood storage and/or rejuvenating composition. In one embodiment, the composition includes D-ribose and L-arginine and/or D-arginine (and preferably L-arginine). Optionally, the composition can further include one or more of sodium pyruvate, an inorganic phosphate, and inosine. In preferred embodiments, the composition is an aqueous solution. In preferred embodiments, the composition is an aqueous composition having a pH of 6 to 8.5. Methods of using such compositions are also disclosed.

In another embodiment, the blood storage and/or rejuvenating composition includes: 75 to 1500 mM L-arginine and/or D-arginine (and preferably L-arginine); and 75 to 1500 mM inosine, wherein the composition is an aqueous solution. Optionally, the composition can further include D-ribose at a concentration of, for example, 75 to 1500 mM. Optionally, the composition can further include sodium pyruvate at a concentration of, for example, 75 to 1500 mM. Optionally, the composition can further include an inorganic phosphate at a concentration of, for example, 75 to 1500 mM. When used to store and/or rejuvenate blood, the composition is typically diluted approximately 30-fold to provide a final concentration of 2.5 to 50 mM L-arginine and/or D-arginine (and preferably L-arginine); 2.5 to 50 mM inosine; and optionally 2.5 to 50 mM D-ribose, 2.5 to 50 mM sodium pyruvate, and/or 2.5 to 50 mM inorganic phosphate.

In certain preferred embodiments, the blood storage and/or rejuvenating composition includes: 150 to 900 mM L-arginine and/or D-arginine (and preferably L-arginine); and 150 to 900 mM inosine, and the composition is an aqueous solution. Optionally, the composition can further include D-ribose at a concentration of, for example, 150 to 900 mM. Optionally, the composition can further include sodium pyruvate at a concentration of, for example, 150 to 900 mM. Optionally, the composition can further include an inorganic phosphate at a concentration of, for example, 150 to 900 mM. When used to store and/or rejuvenate blood, the composition is typically diluted approximately 30-fold to provide a final concentration of 5 to 30 mM L-arginine and/or D-arginine (and preferably L-arginine); and 5 to 30 mM inosine; and optionally 5 to 30 mM D-ribose, 5 to 30 mM sodium pyruvate, and/or 5 to 30 mM inorganic phosphate.

In other preferred embodiments, the blood storage and/or rejuvenating composition includes: 300 to 600 mM L-arginine and/or D-arginine (and preferably L-arginine); and 300 to 600 mM inosine, and the composition is an aqueous solution. Optionally, the composition can further include D-ribose at a concentration of, for example, 300 to 600 mM. Optionally, the composition can further include sodium pyruvate at a concentration of, for example, 300 to 600 mM. Optionally, the composition can further include an inorganic phosphate at a concentration of, for example, 300 to 600 mM. When used to store and/or rejuvenate blood, the composition is typically diluted approximately 30-fold to provide a final concentration of 10 to 20 mM L-arginine and/or D-arginine (and preferably L-arginine); and 10 to 20 mM inosine; and optionally 10 to 20 mM D-ribose, 10 to 20 mM sodium pyruvate, and/or 10 to 20 mM inorganic phosphate.

In certain embodiments, the molar ratio of L-arginine to inosine is 0.5:1 to 1.5:1. In other certain embodiments, the molar ratio of L-arginine to inosine is 0.8:1 to 1.2:1. In certain preferred embodiments, the molar ratio of L-arginine to inosine is 1:1.

In another embodiment, the blood storage and/or rejuvenating composition includes: 300 mM L-arginine; 300 mM inosine; 300 mM D-ribose; 300 mM sodium pyruvate; and 300 mM inorganic phosphate, wherein the composition is an aqueous solution. When used to store and/or rejuvenate blood, the composition is typically diluted approximately 30-fold to provide a final concentration of 10 mM L-arginine; 10 mM inosine; 10 mM D-ribose; 10 mM sodium pyruvate; and 10 mM inorganic phosphate.

In certain embodiments, a blood storage and/or rejuvenating composition as described herein can further include one or more of sodium chloride, dextrose, adenine, mannitol, sodium citrate, and citric acid.

For one example, the blood storage and/or rejuvenation composition can be an additive solution that includes L-arginine, inosine, D-ribose, sodium pyruvate, inorganic phosphate, sodium chloride, dextrose, adenine, and mannitol. Such an additive solution is particularly useful for storing and/or rejuvenating blood containing an anticoagulant selected from the group consisting of ACD, CPD, CPDA-1, and combinations thereof.

For another example, the blood storage and/or rejuvenating composition can be an additive solution that includes L-arginine, inosine, D-ribose, sodium pyruvate, inorganic phosphate, sodium chloride, dextrose, adenine, sodium citrate, and citric acid. Such an additive solution is particularly useful for storing and/or rejuvenating blood containing CP2D anticoagulant.

The compositions described herein can be used, for example, in a method of storing blood. In certain embodiments, the method includes contacting RBCs (e.g., packed RBCs or in whole blood) with a blood storage and/or rejuvenating composition as described herein.

Alternatively, or in addition to, the compositions described herein can be used, for example, in a method of rejuvenating blood (e.g., packed RBCs or in whole blood). In certain embodiments, the method includes contacting RBCs with a blood storage and/or rejuvenating composition as described herein.

In some embodiments, the blood storage and/or rejuvenating compositions disclosed herein can be in the form of additive solutions that can be added to RBCs upon collection of the whole blood; to RBCs before, during, and/or after the plasma is removed; and/or to packed RBCs before, during, and/or after storage.

In certain preferred embodiments, the method of rejuvenating blood includes: providing RBCs (e.g., packed RBCs or in whole blood) having a 2,3-DPG value lower than the value for freshly drawn blood; and mixing the RBCs with a blood storage and/or rejuvenating composition under conditions effective to increase the 2,3-DPG value, wherein the blood storage and/or rejuvenating composition includes L-arginine and/or D-arginine. In certain embodiments, conditions effective to increase the 2,3-DPG value include incubating the cells in the blood storage and/or rejuvenating composition at a temperature of 4° C. to 37° C., and in certain preferred embodiments at a temperature of room temperature. In certain embodiments, conditions effective to increase the 2,3-DPG value include incubating the cells in the blood storage and/or rejuvenating composition for a time of at least 10 minutes, in preferred embodiments for a time of 10 minutes to 48 hours, in certain preferred embodiments for a time of 10 minutes to 4 hours, and in other preferred embodiments for a time of 30 minutes to 2 hours. Exemplary conditions effective to increase the 2,3-DPG value include incubating the cells in the blood storage and/or rejuvenating composition at 37° C. for 10 minutes to four hours. Other exemplary conditions effective to increase the 2,3-DPG value include incubating the cells in the blood storage and/or rejuvenating composition at room temperature for 10 minutes to 24 hours, in some embodiments 10 minutes to 8 hours, and in some embodiments 10 minutes to four hours. In preferred embodiments, the blood storage and/or rejuvenating composition includes one or more of the blood storage and/or rejuvenating compositions described herein.

In certain preferred embodiments, the method of rejuvenating blood includes: providing RBCs (e.g., packed RBCs or in whole blood) having an ATP value lower than the value for freshly drawn blood; and mixing the RBCs with a blood storage and/or rejuvenating composition under conditions effective to increase the ATP value, wherein the blood storage and/or rejuvenating composition includes L-arginine and/or D-arginine. In certain embodiments, conditions effective to increase the ATP value include incubating the cells in the blood storage and/or rejuvenating composition at a temperature of 4° C. to 37° C., and in certain preferred embodiments at a temperature of room temperature. In certain embodiments, conditions effective to increase the ATP value include incubating the cells in the blood storage and/or rejuvenating composition for a time of at least 10 minutes, in preferred embodiments for a time of 10 minutes to 48 hours, in certain preferred embodiments for a time of 10 minutes to 4 hours, and in other preferred embodiments for a time of 30 minutes to 2 hours. Exemplary conditions effective to increase the ATP value include incubating the cells in the blood storage and/or rejuvenating composition at 37° C. for 10 minutes to four hours. Other exemplary conditions effective to increase the ATP value include incubating the cells in the blood storage and/or rejuvenating composition at room temperature for 10 minutes to 24 hours, in some embodiments 10 minutes to 8 hours, and in some embodiments 10 minutes to four hours. In preferred embodiments, the blood storage and/or rejuvenating composition includes one or more of the blood storage and/or rejuvenating compositions described herein.

In certain preferred embodiments, the method of rejuvenating blood includes: providing RBCs (e.g., packed RBCs or in whole blood) having a reduced glutathione value lower than the value for freshly drawn blood; and mixing the RBCs with a blood storage and/or rejuvenating composition under conditions effective to increase the reduced glutathione value, wherein the blood storage and/or rejuvenating composition includes L-arginine and/or D-arginine. In certain embodiments, conditions effective to increase the reduced glutathione value include incubating the cells in the blood storage and/or rejuvenating composition at a temperature of 4° C. to 37° C., and in certain preferred embodiments at a temperature of room temperature. In certain embodiments, conditions effective to increase the reduced glutathione value include incubating the cells in the blood storage and/or rejuvenating composition for a time of at least 10 minutes, in preferred embodiments for a time of 10 minutes to 48 hours, in certain preferred embodiments for a time of 10 minutes to 4 hours, and in other preferred embodiments for a time of 30 minutes to 2 hours. Exemplary conditions effective to increase the reduced glutathione value include incubating the cells in the blood storage and/or rejuvenating composition at 37° C. for 10 minutes to four hours. Other exemplary conditions effective to increase the reduced glutathione value include incubating the cells in the blood storage and/or rejuvenating composition at room temperature for 10 minutes to 24 hours, in some embodiments 10 minutes to 8 hours, and in some embodiments 10 minutes to four hours. In preferred embodiments, the blood storage and/or rejuvenating composition includes one or more of the blood storage and/or rejuvenating compositions described herein.

In certain preferred embodiments, the method of rejuvenating blood includes: providing RBCs (e.g., packed RBCs or in whole blood) having an oxygen dissociation P50 value lower than the value for freshly drawn blood; and mixing the RBCs with a blood storage and/or rejuvenating composition under conditions effective to increase the oxygen dissociation P50 value, wherein the blood storage and/or rejuvenating composition includes L-arginine and/or D-arginine. In certain embodiments, conditions effective to increase the oxygen dissociation P50 value include incubating the cells in the blood storage and/or rejuvenating composition at a temperature of 4° C. to 37° C., and in certain preferred embodiments at a temperature of room temperature. In certain embodiments, conditions effective to increase the oxygen dissociation P50 value include incubating the cells in the blood storage and/or rejuvenating composition for a time of at least 10 minutes, in preferred embodiments for a time of 10 minutes to 48 hours, in certain preferred embodiments for a time of 10 minutes to 4 hours, and in other preferred embodiments for a time of 30 minutes to 2 hours. Exemplary conditions effective to increase the oxygen dissociation P50 value include incubating the cells in the blood storage and/or rejuvenating composition at 37° C. for 10 minutes to four hours. Other exemplary conditions effective to increase the oxygen dissociation P50 value include incubating the cells in the blood storage and/or rejuvenating composition at room temperature for 10 minutes to 24 hours, in some embodiments 10 minutes to 8 hours, and in some embodiments 10 minutes to four hours. In preferred embodiments, the blood storage and/or rejuvenating composition includes one or more of the blood storage and/or rejuvenating compositions described herein.

In another aspect, the present disclosure further provides methods of improving the antioxidant defense of stored RBCs.

In one embodiment, the method includes contacting RBCs with a blood storage and/or rejuvenating composition as described herein.

In another embodiment, the method includes contacting a composition including RBCs and an anticoagulant with an additive solution as described herein, wherein the anticoagulant is selected from the group consisting of ACD, CPD, CPDA-1, and combinations thereof.

In another embodiment, the method includes contacting a composition including RBCs and an anticoagulant with an additive solution as described herein, wherein the anticoagulant is CP2D.

By increasing 2,3-DPG concentration in stressed RBCs, it is postulated RBC storage and/or rejuvenating compositions as disclosed herein will decrease oxygen affinity and increase oxygen delivery to affected tissue following transfusion. Further, by maintaining cellular energetics, it is hypothesized that the storage and/or rejuvenating compositions disclosed herein will decrease cell fragility and increase deformability, thereby improving flow through the capillaries. The net result will be a decrease in storage lesions and greater oxygen delivery to affected tissue following transfusion.

In preferred embodiments, the blood storage and/or rejuvenating compositions disclosed herein have the additional benefit of preserving and enhancing the antioxidant defense of the stored red cells, thereby reducing the storage lesion. It is believed that the storage solution will positively impact blood banking and transfusion techniques by providing a composition that minimizes the effect of RBC storage lesions and improves functionality of stored RBCs.

The functional changes in RBCs caused by loss of 2,3-DPG and intracellular ATP are well documented. RBC hypothermic storage has led to the success of up to 42 day storage of RBCs. However, some current storage solutions do not prevent the time dependent oxidative assault on the red cells that lead to the formation of reactive oxygen species, attachment of denatured hemoglobin to membrane phospholipids, and the release of hemoglobin containing membrane microvesicles throughout storage (Kanias et al., *FEBS Journal*, 2009; 277:343-356).

Spontaneous lipid peroxidation has been reported as one of the main causes for erythrocyte aging. See, for example, Jóźwik et al., *Clin. Chim. Acta.*, 1997 Nov. 28; 267(2):129-142; Dormandy, *Br. J. Haematol*, 1971; 20:457-461; Halliwell et al., *Biochem. J.*, 1984; 219:1-14; Chiu et al., *Seminars in Hematology*, 1989; 26:257-276; Knight et al., *Transfusion*, 1992; 32:354-357; and Jain, *Biochim. Biophys. Acta*, 1988; 937:205-210. Oxidation in general is a significant cause of cellular damage and results in the accumulation of reactive end products of lipid oxidation, modification of membrane protein and nucleic acid structure, and reduction of enzymatic activity (Dumaswala et al., *Free Rad. Res.*, 2000, 33:517-529). In healthy erythrocytes, significant oxidative damage is prevented by the very efficient antioxidant system, consisting of small antioxidant compounds such as glutathione (GSH), vitamin E, vitamin C, and enzymes such as GSH-peroxidase (GSH-PX), catalase, and superoxide dismutase (SOD). Reduced GSH, together with GSH-PX, is one of the major scavengers of activated oxygen species in RBCs. GSH accounts for 90% of the intracellular non-protein thiols and is therefore an important intracellular reducing agent for RBCs. It has been reported that hypothermic storage of RBCs induces a time dependent loss of GSH, which in turn leads to an increase in potentially toxic peroxides (e.g., hydrogen peroxide). In addition, it has been shown that the decline in GSH concentration is accompanied with a decrease in GSH-PX and an increase in oxidative modification of membrane lipids and proteins, including malondialdehyde (MDA) (Deneke et al., *Am. J. Physiol. Lung Cell. Mol. Physiol.*, 1989; 257:L163-L173). In preferred embodiments, the blood storage and/or rejuvenating compositions disclosed herein combat the oxidative assault on RBCs during hypothermic storage.

In preferred embodiments, the blood storage and/or rejuvenating compositions disclosed herein maintain the GSH levels of the hypothermic stored RBCs, which in turn preserve the antioxidant activity in stored blood. In preferred embodiments, the blood storage and/or rejuvenating compositions disclosed herein include D-Ribose in a solution, which can allow for bypassing the rate limiting steps of the pentose phosphate pathway of glucose metabolism to stimulate PRPP synthesis.

The present invention is illustrated by the following examples. It is to be understood that the particular examples, materials, amounts, and procedures are to be interpreted broadly in accordance with the scope and spirit of the invention as set forth herein.

EXAMPLES

Example 1

A storage and/or rejuvenating composition that includes D-ribose, inosine, sodium pyruvate, and inorganic phosphate, all at a 300 mM concentration as a slurry was prepared. When used to store and/or rejuvenate RBCs, the slurry is diluted 30-fold to a final concentration of 10 mM to form a solution. The composition exhibits significant results in restoring 2,3-DPG levels in stored RBCs and increasing the ATP content from the baseline value. In a study, RBCs were collected and stored for an average of 21 days at 4° C. according to standard blood banking practice. Various RBC storage and/or rejuvenating compositions were added to the 21-day old stored RBCs and held at 37° C. for one to four hours before being tested for 2,3-DPG concentrations. 2,3-DPG levels were measured in all the examples using a diagnostic 2,3-diphosphoglycerate (DPG) kit available from Roche Diagnostics Corp. (Cat. #10148334001). A normal 2,3-DPG concentration of RBC immediately upon harvest is 4.0 µmol/ml. Following storage the average 2,3-DPG concentration fell to 0.17 µmol/ml (Table 1). The addition of RBC storage and/or rejuvenating composition restored the concentration to greater than 50% of normal post-harvest level. An increase to 1.0 µmol/ml is considered a significant improvement. This series of experiments demonstrated a RBC storage and/or rejuvenating composition increased ATP content and 2,3-DPG levels. The practicality of the solution for adoption in blood bank practice may be limited, however, due to the low solubility of inosine as well as the need for warming of the blood (e.g., for one hour) prior to transfusion.

TABLE 1

2,3-DPG Level of Stored RBCs with RBC Storage and/or Rejuvenating Composition

| Time Point (Hours) | Average 2,3-DPG (μmol/ml) | Range (μmol/ml) | N = | % ATP increase |
|---|---|---|---|---|
| 0 | 0.17 | 0.07-0.35 | 5 | |
| 1 | 2.4 | 1.8-3.3 | 10 | 24 |
| 2 | 1.8 | 1.2-2.7 | 10 | 22 |

Experimental protocols were designed to find methods to increase the solubility of inosine. It was found that L-arginine in an equimolecular solution enhanced the inosine solubility such that inosine remained in solution at concentrations above 50 mM at room temperature. A storage and/or rejuvenating composition including 300 mM each of inosine, L-arginine, sodium pyruvate, D-ribose, and inorganic phosphate was diluted 30-fold into 21-day old stored RBCs. One set of stored blood samples was incubated for 60 minutes at room temperature and another was incubated for 60 minutes at 37° C. As shown in Table 2, the L-arginine containing storage and/or rejuvenating compositions successfully restored 2,3-DPG and ATP levels regardless of mode of warming. This result demonstrates the rejuvenation of 2,3-DPG and ATP using room temperature incubation and a solution devoid of problems associated with slurries and washing of the red cells prior to transfusion.

TABLE 2

2,3-DPG and ATP of stored RBC in L-arginine containing solution

| Sample | Average 2,3-DPG (μmol/ml) | Range (μmol/ml) | N = | % ATP increase |
|---|---|---|---|---|
| Control | 0.29 | N.A. | 1 | |
| 60 minutes at 37° C. | 3.2 | 2.9-3.5 | 3 | 29 |
| 60 minutes at Room Temperature | 1.3 | 1.0-1.5 | 3 | 27 |

Example 2

An additional experimental protocol was designed to determine if nucleosides other than inosine can successfully aid in restoring 2,3-DPG and ATP levels and, potentially, reduce formation of the breakdown products, hypoxanthine and uric acid. Guanosine, a purine nucleoside consisting of guanine linked by its N9 nitrogen to the C1 carbon of ribose, was chosen as the test nucleotide. Table 3 presents data obtained using a storage and/or rejuvenating composition including a 10 mM final concentration each of guanosine, sodium pyruvate, inorganic phosphate, and D-ribose.

TABLE 3

2,3-DPG and ATP of stored RBC in a guanosine containing solution

| Time Point (Hours) | Average 2,3-DPG (μmol/ml) | Range (μmol/ml) | N = | % ATP increase |
|---|---|---|---|---|
| Control | 0.25 | N.A. | 1 | |
| 60 minutes at 37° C. | 1.94 | 1.51-2.43 | 3 | 43 |
| 60 minutes at Room Temperature | 0.51 | 0.28-0.83 | 3 | 32 |

The 10 mM guanosine solution was capable of restoring 2,3-DPG levels when heated to 37° C. for 60 minutes. The concentrated guanosine composition was not completely soluble and, upon dilution, did not restore 2,3-DPG levels following room temperature incubation, although ATP levels were elevated.

Example 3

Table 4 presents data obtained using a storage and/or rejuvenating composition including 10 mM each of inorganic phosphate and D-ribose, and guanosine at the indicated concentration. The solutions did not include sodium pyruvate. Rejuvenation was observed for 60 minutes incubation at 37° C.

TABLE 4

| | 2,3-DPG (μmol/ml) |
|---|---|
| Control | 0.20 |
| 1 mM Guanosine | 0.47 |
| 5 mM Guanosine | 1.30 |
| 10 mM Guanosine | 1.10 |

Example 4

Table 5 presents data obtained using a storage and/or rejuvenating composition including a final concentration of 10 mM each of L-arginine, inosine, D-ribose, sodium pyruvate, and inorganic phosphate. Rejuvenation was observed after 10 minutes and 60 minutes of incubation at 37° C.

TABLE 5

| | 2,3-DPG (μmol/ml) |
|---|---|
| Control | −0.17 |
| 10 minutes at 37° C. | 1.39 |
| 60 minutes at 37° C. | 4.25 |

Example 5

Rejuvenation was not observed for 60 minutes incubation at 37° C. when inosine was replaced with varying concentrations of inosine monophosphate in a storage and/or rejuvenating composition including 10 mM each of D-ribose, sodium pyruvate, and inorganic phosphate.

Example 6

Rejuvenation was not observed for 60 minutes incubation at 37° C. when inosine was replaced with varying concentrations of ribose-5-phosphate in a storage and/or rejuvenating composition including 10 mM each of D-ribose, sodium pyruvate, and inorganic phosphate.

Example 7

Rejuvenation was not observed for 10 minutes incubation at 4° C. in a storage and/or rejuvenating composition including 10 mM each of inosine, D-ribose, sodium pyruvate, and inorganic phosphate.

Example 8

Oxygen Dissociation Evaluation

An oxygen dissociation curve (ODC) provides a measurement of the percent saturation of hemoglobin at various partial pressures of oxygen. The ODC provides a P50 value which is a measurement of the pressure at which the erythrocytes are fifty percent saturated with oxygen.

The discovery of the S-shaped $O_2$ equilibrium curve and the Bohr effect in 1904 stimulated fertile and continued research into respiratory functions of blood and allosteric mechanisms in haemoglobin (Hb). The Bohr effect (influence of $pH/CO_2$ on $HbO_2$ affinity) and the reciprocal Haldane effect (influence of $HbO_2$ saturation on $H^+/CO_2$ binding) originate in the Hb oxy-deoxy conformational change and allosteric interactions between $O_2$ and $H^+/CO_2$ binding sites. In steady state, $H^+$ is passively distributed across the RBC membrane, and intracellular pH (pHi) changes are related to changes in extracellular pH, Hb—$O_2$ saturation and RBC organic phosphate content. As the Hb molecule shifts between the oxy and deoxy conformation in arterial-venous gas transport, it delivers $O_2$ and takes up $CO_2$ and $H^+$ in tissue capillaries (Jensen, *Acta Physiol Scand*, November 2004, 182(3):215-27).

RBC storage and/or rejuvenating compositions preferably elevate ATP content, and increase 2,3-DPG levels. However, it is also desirable that the storage and/or rejuvenating compositions result in increased oxygen dissociation from the red cells to tissue. Presently disclosed RBC storage and/or rejuvenating compositions have been shown to be effective in enhancing oxygen dissociation.

2,3-DPG lowers the binding affinity of $O_2$ for hemoglobin; this shifts the curve to the right. The effect of 2,3-DPG on oxygen dissociation is illustrated in FIG. 1.

P50 values were assessed using the Hemox Analzer (TCS Medical, South Hampton, Pa.). A summary of evaluation of oxygen dissociation under room temperature and 37° C. is shown in Table 6. In all tests listed below the following storage and/or rejuvenating composition was evaluated: 10 mM of the following (ribose, sodium pyruvate, L-arginine, inorganic phosphate, inosine). Bags evaluated were CDPA-AS1.

TABLE 6

| Bag | Temp | Time | P50 |
| --- | --- | --- | --- |
| 1 | RT | 15 minutes | 8.3 |
| 2 | RT | 15 minutes | 9.1 |
| 3 | RT | 15 minutes | 8.8 |
| 4 | RT | 15 minutes | 7.9 |
| Control | | | 3.1 |
| 1 | RT | 60 minutes | 12.1 |
| 2 | RT | 60 minutes | 10.4 |
| 3 | RT | 60 minutes | 13.2 |
| 4 | RT | 60 minutes | 12.6 |
| Control | | | 2.9 |
| 1 | 37° C. | 60 minutes | 19.2 |
| 2 | 37° C. | 60 minutes | 31.4 |
| 3 | 37° C. | 60 minutes | 26.7 |
| 4 | 37° C. | 60 minutes | 38.1 |
| Control | | | 3.6 |

Example 9

Storage Experiment

A 30× concentration stock solution of D-ribose, inosine, L-arginine, sodium pyruvate, and inorganic phosphate was prepared in a citrate phosphate dextrose anticoagulant solution (AS1, Fenwal Inc., Lake Zurich, Ill.) to produce Solution A, which was formulated so as to provide a final blood concentration of 10 mM D-ribose, 10 mM inosine, 10 mM L-arginine, 10 mM sodium pyruvate, and 10 mM inorganic phosphate. The citrate phosphate dextrose anticoagulant solution reportedly contained 1.8 g trisodium citrate, 1.78 g dextrose, 209 mg citric acid, and 155 mg monobasic sodium phosphate per 70 ml solution. The pH of solution A was adjusted to 6.25 using HCl.

Human blood from a normal donor was collected in Solution A in a 1:8 volume ratio of Solution A to blood, by prefilling 2.5 mL of Solution A in a syringe, and then collecting 20 mL of donor blood directly into the Solution A containing syringe. As a control, samples were prepared using AS1 additive solution instead of Solution A.

The samples were heat sealed in 20 ml bags and stored at 4° C.

2,3-DPG levels, pH, ATP, and P50 were measured as described herein and the results are shown in Table 7 and FIGS. 2-5. Reduced glutathione was measured using the Bioxytech GSH-420 kit from Oxis Research.

TABLE 7

| | 2,3-DPG (mmole 2,3-DPG/liter erythrocytes) | pH | ATP % Baseline | Reduced Glutathione % | P50 (mm Hg) |
| --- | --- | --- | --- | --- | --- |
| Day 0 Control | 3.2 | 7.3 | 100 | 100 | 35 |
| Day 0 Solution A | 3.2 | 7.3 | 100 | 100 | 35 |
| Day 7 Control | 1.8 | 7.3 | 82 | 87 | 16.6 |
| Day 7 Solution A | 3.2 | 7.3 | 94 | 142 | 37 |
| Day 14 Control | 0.43 | 7.1 | 79 | 79 | 14.2 |
| Day 14 Solution A | 3.2 | 7.1 | 89 | 110 | 29 |
| Day 21 Control | 0.35 | 7 | 45 | 63 | 2.8 |
| Day 21 Solution A | 2.9 | 7.1 | 83 | 102 | 21.2 |

Example 10

Rejuvenation Experiment

Outdated packed RBCs (45-47 days) were obtained from American Red Cross (Chicago, Ill.) that contained either AS3 or AS5 as an additive.

A 30× concentration stock solution of D-ribose, inosine, L-arginine, sodium pyruvate, and inorganic phosphate was prepared in an AS3 additive (Pall), to produce Solution B, which was formulated so as to provide a final blood concentration of 10 mM D-ribose, 10 mM inosine, 10 mM L-arginine, 10 mM sodium pyruvate, and 10 mM inorganic phosphate. 10 mL of Solution B was added to 300 mL of 47 day old packed RBCs. As controls, samples were prepared using AS3 additive instead of Solution B.

A 30× concentration stock solution of D-ribose, inosine, L-arginine, sodium pyruvate, and inorganic phosphate was prepared in an AS5 additive (Terumo), to produce Solution C, which was formulated so as to provide a final blood concentration of 10 mM D-ribose, 10 mM inosine, 10 mM L-arginine, 10 mM sodium pyruvate, and 10 mM inorganic phosphate. 10 mL of Solution C was added to 300 mL of 45 day old packed RBCs. As controls samples were prepared using AS5 additive instead of Solution C.

The rejuvenation conditions were 37° C. for 60 minutes with mixing. 2,3-DPG levels were measured and the results are shown in Table 8.

TABLE 8

| | | | 2,3-DPG (mmole 2,3-DPG/liter erythrocytes) |
|---|---|---|---|
| 47 day old packed RBC with CPD anticoagulant | Solution B | Bag 1 | 2.49 |
| | Solution B | Bag 2 | 2.99 |
| | | Average | 2.74 |
| | Control (AS3) | Bag 1 | 0.26 |
| | Control (AS3) | Bag 2 | 0.29 |
| | | Average | 0.28 |
| 45 day old packed RBC with CP2D anticoagulant | Solution C | Bag 1 | 2.92 |
| | Solution C | Bag 2 | 4.01 |
| | | Average | 3.46 |
| | Control (AS5) | Bag 1 | 0.41 |
| | Control (AS5) | Bag 2 | 0.76 |
| | | Average | 0.59 | phosphate. Human blood from a normal donor was collected in Solution D in a 1:8 volume ratio of Solution D to blood, by prefilling 2.5 mL of Solution D in a syringe, and then collecting 20 mL of donor blood directly into the Solution D containing syringe.

A 30× concentration stock solution of D-ribose, inosine, L-arginine, sodium pyruvate, and inorganic phosphate was prepared in an AS5 additive solution (Terumo) to produce Solution E, which was formulated so as to provide a final blood concentration of 10 mM D-ribose, 10 mM inosine, 10 mM L-arginine, 10 mM sodium pyruvate, and 10 mM inorganic phosphate. Human blood from a normal donor was collected in Solution E in a 1:8 volume ratio of Solution E to blood, by prefilling 2.5 mL of Solution E in a syringe, and then collecting 20 mL of donor blood directly into the Solution E containing syringe.

As a control, samples were prepared using AS1 additive solution instead of either Solution D or Solution E.

The samples were heat sealed in 20 ml bags and stored at 4° C.

2,3-DPG levels, pH, P50, and ATP were measured as described herein and the results are shown in Table 9 and FIGS. 6-9. Reduced glutathione was measured using the Bioxytech GSH-420 kit from Oxis Research.

TABLE 10

| | Day 0 | Day 7 | Day 14 | Day 21 | Day 28 | Day 35 | Day 42 | Day 49 |
|---|---|---|---|---|---|---|---|---|
| Solution D (AS3) | | | | | | | | |
| 2,3-DPG (mmole 2,3-DPG/liter erythrocytes) | 3.2 | 3.2 | 3 | 2.8 | 2.6 | 2.1 | 2 | 1.3 |
| ATP (% Baseline) | 100 | 106 | 109 | 94 | 96 | 89 | 91 | 79 |
| pH | 6.9 | 6.9 | 6.7 | 6.6 | 6.5 | 6.5 | 6.4 | 6.2 |
| Reduced Glutathione (%) | 100 | | 109 | | 89 | | 78 | 54 |
| P50 (mm Hg) | 16.2 | 15.3 | 15.1 | 13.9 | 12.1 | 12.6 | 12 | |
| Solution E (AS5) | | | | | | | | |
| 2,3-DPG (mmole 2,3-DPG/liter erythrocytes) | 2.8 | 3.1 | 2.7 | 2.7 | 2.3 | 2 | 2.1 | 1.6 |
| ATP (% Baseline) | 100 | 101 | 93 | 95 | 91 | 84 | 88 | 61 |
| pH | 7.2 | 7 | 6.9 | 6.8 | 6.6 | 6.5 | 6.3 | 6.1 |
| Reduced Glutathione (%) | 100 | | 104 | | 95 | | 71 | 46 |
| Control | | | | | | | | |
| 2,3-DPG (mmole 2,3-DPG/liter erythrocytes) | 3.2 | 1.4 | 0.5 | | | | | |
| ATP (% Baseline) | 100 | 95 | 91 | 79 | 79 | 71 | 73 | 66 |
| pH | 6.9 | 6.9 | 6.9 | 6.7 | 6.5 | 6.5 | 6.3 | 6.3 |
| Reduced Glutathione (%) | 100 | | 59 | | 46 | | 29 | 22 |
| P50 (mm Hg) | 16.2 | 4.1 | 1 | | | | | |

Example 11

Storage Experiment

Storage experiments were conducted as described in Example 9, except that AS3 and AS5 additive solutions were used instead of the AS1 additive solution, as described herein below.

A 30× concentration stock solution of D-ribose, inosine, L-arginine, sodium pyruvate, and inorganic phosphate was prepared in an AS3 additive solution (Pall) to produce Solution D, which was formulated so as to provide a final blood concentration of 10 mM D-ribose, 10 mM inosine, 10 mM L-arginine, 10 mM sodium pyruvate, and 10 mM inorganic The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A blood storage and/or rejuvenating composition comprising:

D-ribose, inosine, sodium pyruvate, inorganic phosphate, and L-arginine and/or D-arginine.

2. The composition of claim 1 wherein the composition is an aqueous solution.

3. A blood storage and/or rejuvenating composition according to claim 1 further comprising one or more of sodium chloride, dextrose, adenine, mannitol, sodium citrate, and citric acid.

4. The blood storage and/or rejuvenating composition of claim 3 wherein the composition is an additive solution comprising L-arginine, inosine, D-ribose, sodium pyruvate, inorganic phosphate, sodium chloride, dextrose, adenine, and mannitol.

5. The blood storage and/or rejuvenating composition of claim 3 wherein the composition is an additive solution comprising L-arginine, inosine, D-ribose, sodium pyruvate, inorganic phosphate, sodium chloride, dextrose, adenine, sodium citrate, and citric acid.

6. A blood storage and/or rejuvenating composition comprising:
   75-1500 mM D-ribose,
   75-1500 mM L-arginine,
   75 to 1500 mM inosine,
   sodium pyruvate, and
   inorganic phosphate,
   wherein the composition is an aqueous solution.

7. The composition of claim 6 wherein the molar ratio of L-arginine to inosine is 0.5:1 to 1.5:1.

8. The composition of claim 7 wherein the molar ratio of L-arginine to inosine is 0.8:1 to 1.2:1.

9. The composition of claim 8 wherein the molar ratio of L-arginine to inosine is 1:1.

10. The composition of claim 6 wherein the concentration of the sodium pyruvate is 75 to 1500 mM.

11. The composition of claim 6 wherein the concentration of the inorganic phosphate is 75 to 1500 mM.

12. A blood storage and/or rejuvenating composition comprising:
   300 mM L-arginine;
   300 mM inosine;
   300 mM D-ribose;
   300 mM sodium pyruvate; and
   300 mM inorganic phosphate,
   wherein the composition is an aqueous solution.

13. A method of storing blood, the method comprising contacting red blood cells with a blood storage and/or rejuvenating composition according to claim 1.

14. The method of claim 13 wherein the red blood cells are packed red blood cells or in whole blood.

15. A method of rejuvenating blood, the method comprising contacting red blood cells with a blood storage and/or rejuvenating composition according to claim 1.

16. The method of claim 15 wherein the red blood cells are packed red blood cells or in whole blood.

17. The method of claim 15 wherein the red blood cells have been damaged by blood fractionation, a filtration procedure, or a pathogen inactivation treatment.

18. The method of claim 17 wherein the filtration procedure comprises leukofiltration.

19. A method of rejuvenating blood, the method comprising:
   providing red blood cells having a 2,3-diphosphoglycerate value lower than the value for freshly drawn blood;
   mixing the red blood cells with a blood storage and/or rejuvenating composition according to claim 1 under conditions effective to increase the 2,3-diphosphoglycerate value.

20. The method of claim 19 wherein conditions effective comprise incubating the cells in the blood storage and/or rejuvenating composition at a temperature of 4° C. to 37° C.

21. The method of claim 20 wherein the temperature is room temperature.

22. The method of claim 19 wherein conditions effective comprise incubating the cells in the blood storage and/or rejuvenating composition for a time of at least 10 minutes.

23. The method of claim 22 wherein the time is 10 minutes to 48 hours.

24. The method of claim 23 wherein the time is 10 minutes to 4 hours.

25. The method of claim 24 wherein the time is 30 minutes to 2 hours.

26. The method of any claim 19 wherein the red blood cells are packed red blood cells or in whole blood.

27. The method of claim 19 wherein the provided red blood cells have been damaged by blood fractionation, a filtration procedure, or a pathogen inactivation treatment.

28. The method of claim 27 wherein the filtration procedure comprises leukofiltration.

29. A method of rejuvenating blood, the method comprising:
   providing red blood cells having an adenosine triphosphate value lower than the value for freshly drawn blood;
   mixing the red blood cells with a blood storage and/or rejuvenating composition according to claim 1 under conditions effective to increase the adenosine triphosphate value.

30. The method of claim 29 wherein the provided red blood cells have been damaged by blood fractionation, a filtration procedure, or a pathogen inactivation treatment.

31. The method of claim 30 wherein the filtration procedure comprises leukofiltration.

32. A method of rejuvenating blood, the method comprising:
   providing red blood cells having a reduced glutathione value lower than the value for freshly drawn blood;
   mixing the red blood cells with a blood storage and/or rejuvenating composition according to claim 1 under conditions effective to increase the reduced glutathione value.

33. The method of claim 32 wherein the provided red blood cells have been damaged by blood fractionation, a filtration procedure, or a pathogen inactivation treatment.

34. The method of claim 33 wherein the filtration procedure comprises leukofiltration.

35. A method of rejuvenating blood, the method comprising:
   providing red blood cells having an oxygen dissociation P50 value lower than the value for freshly drawn blood;
   mixing the red blood cells with a blood storage and/or rejuvenating composition according to claim 1 under conditions effective to increase the oxygen dissociation P50 value.

36. The method of claim 35 wherein the provided red blood cells have been damaged by blood fractionation, a filtration procedure, or a pathogen inactivation treatment.

37. The method of claim 36 wherein the filtration procedure comprises leukofiltration.

38. A method of improving the antioxidant defense of stored red blood cells, the method comprising contacting red blood cells with a blood storage and/or rejuvenating composition according to claim 1.

39. A method of storing and/or rejuvenating blood, the method comprising contacting a composition comprising red blood cells and an anticoagulant with a blood storage and/or rejuvenating composition according to claim 4, wherein the anticoagulant is selected from the group consisting of ACD, CPD, CPDA-1, and combinations thereof.

40. The method of claim 39 wherein the red blood cells have been damaged by blood fractionation, a filtration procedure, or a pathogen inactivation treatment.

41. The method of claim 40 wherein the filtration procedure comprises leukofiltration.

42. A method of improving the antioxidant defense of stored red blood cells, the method comprising contacting a composition comprising red blood cells and an anticoagulant with a blood storage and/or rejuvenating composition according to claim 4, wherein the anticoagulant is selected from the group consisting of ACD, CPD, CPDA-1, and combinations thereof.

43. A method of storing and/or rejuvenating blood, the method comprising contacting a composition comprising red blood cells and an anticoagulant with a blood storage and/or rejuvenating composition according to claim 5, wherein the anticoagulant is CP2D.

44. The method of claim 43 wherein the red blood cells have been damaged by blood fractionation, a filtration procedure, or a pathogen inactivation treatment.

45. The method of claim 44 wherein the filtration procedure comprises leukofiltration.

46. A method of improving the antioxidant defense of stored red blood cells, the method comprising contacting a composition comprising red blood cells and an anticoagulant with a blood storage and/or rejuvenating composition according to claim 5, wherein the anticoagulant is CP2D.

47. A blood storage and/or rejuvenating composition comprising:
  75 to 1500 mM D-ribose;
  75 to 1500 mM L-arginine;
  75 to 1500 mM inosine;
  75 to 1500 mM sodium pyruvate; and
  75 to 1500 mM inorganic phosphate,
  wherein the composition is an aqueous solution.

* * * * *